United States Patent
Kraus, Jr. et al.

(10) Patent No.: US 6,470,220 B1
(45) Date of Patent: Oct. 22, 2002

(54) DIAGNOSIS AND TREATMENT OF CANCERS USING IN VIVO MAGNETIC DOMAINS

(75) Inventors: Robert H. Kraus, Jr., Los Alamos, NM (US); Don M. Coates, Santa Fe, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/538,113

(22) Filed: Mar. 29, 2000

Related U.S. Application Data
(60) Provisional application No. 60/126,988, filed on Mar. 29, 1999.

(51) Int. Cl.[7] ............................ A61F 2/00; A61F 17/52
(52) U.S. Cl. ...................... 607/103; 600/9; 600/12
(58) Field of Search ................................ 607/100, 101, 607/103; 600/9, 12

(56) References Cited

U.S. PATENT DOCUMENTS

| | | | |
|---|---|---|---|
| 4,106,488 A | 8/1978 | Gordon | 128/1 R |
| 4,136,683 A | 1/1979 | Gordon | 128/2 H |
| 4,303,636 A | 12/1981 | Gordon | 424/1 |
| 4,569,836 A | 2/1986 | Gordon | 424/1.1 |
| 4,590,922 A | 5/1986 | Gordon | 128/1.3 |
| 4,731,239 A | 3/1988 | Gordon | 424/9 |
| 4,735,796 A | 4/1988 | Gordon | 424/9 |
| 5,043,101 A | 8/1991 | Gordon | 252/408.1 |
| 5,197,940 A * | 3/1993 | Sievert et al. | 600/9 |
| 5,427,767 A * | 6/1995 | Kresse et al. | 424/9.32 |
| 5,604,112 A | 2/1997 | Crane et al. | 435/29 |
| 5,622,686 A | 4/1997 | Gordon et al. | 420/9.32 |
| 5,735,279 A * | 4/1998 | Klaveness et al. | |
| 6,048,515 A * | 4/2000 | Kresse et al. | 424/9.322 |
| 6,149,576 A * | 11/2000 | Gray et al. | 600/10 |
| 6,167,313 A * | 12/2000 | Gray et al. | 607/103 |

* cited by examiner

Primary Examiner—Roy D. Gibson
(74) Attorney, Agent, or Firm—Bruce H. Cottrell (57) ABSTRACT

A method of detecting and treating tumors within a subject is disclosed together with a process for the non-invasive measurement of tissue temperature within a subject.

3 Claims, 2 Drawing Sheets

DIAGNOSIS AND TREATMENT OF CANCERS USING IN VIVO MAGNETIC DOMAINS

This application claims the benefit of U.S. Provisional Application No. 60/126,988 filed Mar. 29, 1999.

FIELD OF THE INVENTION

The present invention relates to a process for non-invasive, non-ionizing diagnostic and treatment applications for cancers such as breast cancer and more generally for any body cells or biological species that can be targeted by an appropriate binding moiety. More particularly, the present invention relates to non-invasive, non-ionizing diagnostic applications involving the delivery of magnetic markers and the in vivo manipulation of the magnetic domains of such magnetic markers. The present invention further relates to a process for the non-invasive measurement of temperature of tissue through the measurement of Barkhausen noise associated with magnetic domains delivered to such tissue. The present invention is the result of a contract with the Department of Energy (Contract No. W-7405-ENG-36).

BACKGROUND OF THE INVENTION

Breast cancer is a serious national problem that will affect approximately twelve percent of women in their lifetimes. Breast cancer is presently the second leading cause of death in women in the U.S. and is one of the most publicly visible and diagnostically investigated diseases. Although probably the most common diagnostic used, physical (both self- or physician administered) examinations are generally a poor diagnostic method as only well developed tumors will be detected. Even palpable changes in breast tissue are poor indicators of the existence of a tumor with an accuracy rate of only between about 60 and 85 percent. Malignant palpable tumors are also typically well developed and thus have poor prognostic outcomes compared with tumors that have been identified early, before they become palpable. For these reasons, mammography or other diagnostic techniques that enable earlier detection of breast cancer are essential to increase both the diagnostic reliability and prognostic outcome.

Mammography is the most common method used to screen women over 40 and younger women in a high-risk group for early detection. Mammography is one of the most powerful and widely used tools for early diagnosis of breast cancer. It has limitations, however, such as for women who have mammographically positive breast tissue resulting from scar tissue from previous radiation therapy, injury or surgery. Mammographically distinguishing between benign and malignant abnormalities is also difficult. Due to the various limitations of the present diagnostic techniques, work has continued on improved diagnostic systems.

Alternatives to mammography (as well as other forms of cancer) are currently being explored including magnetic resonance imaging (MRI), positron emission tomography (PET), and scintimammography. MRI has shown potential for detection of breast cancer, however it remains an experimental tool that typically requires using contrast agents and there exists no standardization at this date. $F^{18}$-(2)-FDG is widely used in PET studies and shows evidence from in vitro studies that it may accumulate in breast cancer cells. The most significant impediments to PET are the extremely high cost of the instrumentation and associated cyclotron, the limited availability of these machines, and the collateral radiation dose associated with this technique. Scintimammography is becoming a principal alternative to mammography where additional confirmation is needed, or mammography simply is not yielding satisfactory results. The method is achieving considerable success but is largely limited by the significant collateral radiation dose to other organs.

Once malignant tumors are positively identified, the most common treatment is surgical removal of the tumor and any associated lymph nodes through one of a number of forms of breast conserving therapy or mastectomy plus sentinal or general lymph node dissection. These methods result in various degrees of disfigurement, morbidity, and emotional distress. Subsequent to surgery, radiation and/or chemotherapy are used to attempt to eradicate tumor cells that may have migrated from the original cancer site.

Various adjunctive therapies have been proposed and tested including hyperthermia. The literature most commonly refers to hyperthermia as an adjunctive therapy to radiation or chemotherapy. Various methods including microwave radiation and heating of magnetic implants have been used to induce the hyperthermia. The belief is that increasing tissue temperature a few degrees (Celsius) increases metabolism and renders tumor cells more susceptible to radiation and/or chemotherapy. This belief has not been conclusively proven. Microwave radiation has also been used to deposit sufficient energy to cause necrosis of tumor cells (e.g. kill the tumor cells) using phasing techniques that focus the energy. This technique, however, causes significant collateral damage in healthy tissue because of substantial energy deposition outside the tumor itself.

Klaveness et al. (U.S. Pat. No. 5,735,279) have described use of SQUIDS for magnetometric imaging of a body using ferromagnetic, ferrimagnetic or paramagnetic materials. Gordon (U.S. Pat. Nos. 4,106,488 and 4,735,796) has described treatment of cancer by use of minute particles possessing ferromagnetic, paramagnetic or diamagnetic properties together with application of a high-frequency alternating electromagnetic field to inductively heat intracellular particles. Despite these efforts, a further search for alternative treatments to surgery remains.

An object of the present invention is a diagnostic and treatment technique for a cancer such as breast cancer wherein a magnetic material attached to a delivery agent is administered to a subject in a manner adapted for localization of a sufficient amount of said magnetic material to a location having cancerous cells, followed by inducement of localized heating of said cancerous cells via manipulation of magnetic domains within said administered magnetic material.

Still another object of the present invention is the use of a intracellular viscous heating process to attain the desired localized heating.

Another object of the present invention is a technique for measuring cellular temperature using measurement of Barkhausen noise.

Still another object of the present invention is the use of the cellular temperature via the measurement of Barkhausen noise for a feedback loop in the treatment technique.

SUMMARY OF THE INVENTION

To achieve the foregoing and other objects, and in accordance with the purposes of the present invention, as embodied and broadly described herein, the present invention provides a method of detecting and treating tumors within a subject including administering a dosage of magnetic material containing substance to a subject, said magnetic material containing substance adapted for preferential attachment to tumor cells; detecting location within said subject of said magnetic material containing substance attached to tumor cells by use of a sensor array including superconducting quantum interference devices; and, manipulating by a low frequency field said magnetic material within said subject such that said magnetic material containing substance undergoes heating whereby tumor cells having said attached magnetic material are heated sufficiently to cause selective necrosis of at least a portion of said tumor cells.

In one embodiment, manipulating magnetic material within said subject includes applying a rotational field to selected portions of said subject whereby said magnetic material containing substance undergoes a rotation to yield viscous heating.

The present invention further provides a process for the non-invasive measurement of tissue temperature within a subject including administering a dosage of magnetic material containing substance to a subject, said magnetic material containing substance adapted for preferential attachment to selected tissue; measuring Barkhausen noise associated with magnetic domains delivered to such selected tissue; and, correlating a tissue temperature with said measured Barkhausen noise.

DETAILED DESCRIPTION

The present invention is concerned with non-invasive, non-ionizing diagnostic and treatment applications such as for non-invasive diagnostic and treatment of cancers such as breast cancer and the like. More generally, the present invention may be concerned with non-invasive, non-ionizing diagnostic and treatment applications for any body cells or biological species that can be targeted by an appropriate binding moiety. Among such body cells may be included blood cells, platelets and the like. Among such biological species may be included various bacterial, viral or fungal entities.

More specifically, the present invention is concerned with non-invasive, non-ionizing diagnostic and treatment applications involving the manipulation of magnetic domains of magnetic markers. The magnetic domains may be manipulated by use of, e.g., coils that emit an electromagnetic field, the field capable of inducing movement of the magnetic domains which can lead to an increase of cellular temperature through viscous heating.

The technique of the present invention for the detection and treatment of cancers is referred to as magnetocarcinotherapy (MCT). MCT utilizes recent advances in magnetic sensor technology combined with biological contrast agent chemistry to detect and localize tumors. If a tumor (or tumors) is identified, MCT enables rapid deposition of energy by a variety of mechanisms to destroy the tumor cells with minimal collateral damage. This technique does not use any form of ionizing radiation or chemotherapy. The MCT technique consists of four primary stages:

1) Binding a cancer-binding agent to a magnetic nano- or micro-particle;
2) Delivery of the magnetic particles to the tumor site by introducing the cancer-binding magnetic particles into the subject bloodstream;
3) Locate tumor(s) by detecting and localizing regions of abnormal uptake and concentration of magnetic particles; and,
4) Inducing tumor necrosis by rapid and focused thermal deposition with minimal collateral damage.

By the term "non-ionizing" is meant without the use of radiation such as x-rays, radioisotopes or the like.

A large number of materials are known to produce magnetic fields and the necessary magnetic field for detection by a sensor system employing superconducting quantum interference devices (SQUIDs) is very small. The materials suitable for production of the needed magnetic fields can include ferromagnetic materials, e.g., iron or iron compounds such as magnetite, a rare-earth/cobalt composition such as samarium cobalt and the like. Magnetic nano- and microparticles are readily available from industry. Magnetites (iron oxide, $Fe_2O_3$) are the most common and widely available and are used in biological applications including bioassay. The "rare-earth magnet" (REM) materials are generally preferred because of the much greater field strength available in these materials. REM materials such as both common forms of samarium-cobalt (Sm—Co) as well as neodymium-iron-boron (Nd—Fe—B) compounds are generally available. These are the most readily available of materials best suited for MCT. Discussions and reviews of the technologies used for producing these extremely small magnetic particles can be found in, e.g., "Permanent Magnetism" by Parker. Batches of permanent magnet materials with uniform sizing are generally preferred.

A number of materials can be used to carry the magnetic material to a tumor site. These materials can be chemical species such as sestamibi (2-hexakis-2-methoxyisobutyl-isonitrile) and the like, or can be any number of biological species such as monoclonal antibodies and the like, e.g., RCC-1 protein (a guanine nucleotide-exchange factor), MDP (methylene diphosphonate), anti-CEA, MOC-31, Leu-M1, Ber-EP4, B72.3, HMFG1 antigen, HMFG2 antigen, BCDF, MA 5, 3C6F9 and the like. Numerous research programs are developing biological contrast agents specific to tumors and cancer cells. A biological contrast agent is a material that is adsorbed in or adheres to cancerous cells. One example of approaches to developing these contrast agents includes biochemicals attracted to cancer cells as a consequence of a specific immune response such as monoclonal antibodies generated against antigens found on. tumors. These approaches have had some success in identifying cancers of the colon, lung, prostate and other tumors of epithelial cell origins. Another example of approaches to developing these contrast agents includes biochemicals that target cell surface receptors with appropriate compounds have also had some success, particularly for estrogen receptors, epidermal growth factor receptors, and somatostatin receptors. Still other examples of approaches to developing these contrast agents include biochemicals specifically attracted to highly metabolic cells (typical of cancer cells); and, biochemicals metabolized by cells (commonly used in greater quantity by cancer cells). For the purpose of the present invention, all of these contrast agents are generally referred to as "cancer binding agents." These cancer binding agents commonly fall into two categories: those highly specific to specific forms of cancers (specific types of cancer cells) because of, e.g., chemical binding and steric effects and those that can be bound to a broad range of cancerous cell types through chemical binding. Agents that target a specific immune response commonly target specific cancer cell types, whereas agents that target rapidly metabolizing cells are usually attracted to a broad range of cancer cell types. Cancer binding agents are commonly used today to deliver chemotherapeutic drugs, carry radioactive atoms for imaging or therapy, or boron atoms for boron neutron capture therapy.

The magnetic materials may be attached to the chemical or biological species used to transport the magnetic material to a tumor site by a process analogous to the preparation of technetium based materials such as Tc-sestamibi as described by Crane et al. in U.S. Pat. No. 5,604,112 and Crane et al., in Eur. J. Nucl. Med., vol. 20, #1, pp. 20–25 (1993) such portions hereby incorporated by reference. In the analogous process, iron particles are substituted for the technetium.

Additionally, the magnetic materials may be selected from among those described by Gordon in U.S. Pat. Nos. 4,106,488; 4,136,683; 4,303,636; 4,569,836; 4,731,239; 4,735,796; 4,590,922; 5,043,101; and 5,622,686, all such disclosures incorporated herein by reference.

Clusters of molecules (nanoparticles) can be used to generate the magnetic field required for MCT. A technique similar to that described by Hainfeld in Science, v. 236, pp. 450–453 (1987) for binding clusters of gold atoms to antibodies can be employed.

Another approach to carry large clusters to cancer cells involves forming buckminsterfullerenes encapsulating the metal complex. "Buckyballs" have already been employed in forming aerosols of $Tc^{99m}$ for ventilation imaging. The advantage of this approach is that the cage can be chemically modified by a variety of strategies to conjugate it to appropriate targeting molecules including antibodies or fragments, peptides, or other molecules of interest. In addition, since the incorporation of the metal complex is by physical, rather than chemical methods, any material with suitable magnetic properties could be used. Since this work does not utilize radionuclides, the opportunity is available to perform more extensive quality control to minimize non-target deposition of the material in vivo.

Still another approach could be to utilize immunoliposomes. In this case, the magnetic material is encapsulated inside liposomes. The liposomes are then derivatized and conjugated to antibodies or their fragments to enhance targeting. Immunoliposomes have been investigated as diagnostic and therapeutic agents. Their success in vivo is dependent on a number of issues. One important technique is to utilize polyethylene glycol to prolong circulation time. This would have no impact on their effectiveness as magneto-contrast agents. This approach has been successfully employed using anti-HER2 antibody against breast cancer.

Magnetic particles are usually obtained in the demagnetized state since the processing occurs well above the Curie point and it is far easier to work with the demagnetized material. The cancer binding agent must be attached to the magnetic particles prior to introduction into the subject. Three methods of attaching the cancer binding agent to the magnetic particles are described.

The magnetic particle may be "encapsulated" within the molecular structure of the cancer binding agent such as "buckyballs" and liposome encapsulation.

Cancer binding agents that are themselves not suitable for encapsulating or coating the magnetic particles must be attached to an intermediate coating attached to the magnetic particle. The use of coatings similar to those used for bioassay experiments will be applied to the magnetic particles to both prevent an autoimmune attack on the particles and to provide suitable chemical binding sites to attach the cancer binding agent to the particle. Coating particles from glass to magnetic (magnetite or $Fe_2O_3$) particles is well known to those skilled in the art. Coatings have been developed and are readily available commercially.

Cancer binding agents may be chemically bound, using organometallic chemistry techniques, directly to the molecular structure of the magnetic particles.

MCT delivers magnetic molecules or particles to tumor sites by binding the magnetic particle or molecule to cancer binding agents as described above. Although the delivery mechanism is similar to scintigraphy, no radioactive materials or ionizing radiation is used in MCT. The cancer binding magnetic particles are introduced into the subject bloodstream and allowed to disperse throughout the subject body. The period of time between injection and magnetic examination (detecting the tumors, see below) will vary for each cancer binding agent. The relative rates of uptake in cancerous and healthy tissue taken together with the relative rates cancerous and healthy tissue clear (eliminate) the magnetic particles will determine the optimal time between injection and magnetic examination. Another benefit of MCT over scintigraphy (and other techniques that use radioactive markers) is that the optimal examination time is not limited by the radioactive half-life of the marker ($Tc^{99m}$ for scintigraphy).

The magnetic particles are prepared in a suspension. Two possible approaches can be used in conjunction with the detection and treatment stages of MCT. The first—and preferable—uses particles that are demagnetized (remnant magnetic field is zero or near-zero). Demagnetized particles are easier to work with because they do not tend to attract one another and cluster together. The suspension will be far easier to work with when performing the chemistry steps (coating the particles, binding the cancer-binding agent), store, and introduce into the subject bloodstream. Appropriate medical considerations will be used when designing the magnetic particle suspension for MCT. A suspension in a Ringers solution is seen as the most likely candidate. Ringers solution suspensions are commonly used in a broad spectrum of medical therapies and experiments involving human subjects.

The second approach uses magnetized particles when in situ magnetization of particles is impractical. This approach will require care in maintaining a uniform suspension in which all of the particles are sufficiently well separated and agitated that agglomeration does not occur. All of the chemistry steps must be conducted with well separated particles. (One possible approach could also be to conduct the chemistry in a micro-machined flow system in which particle spacing is maintained in channels.) Additionally, particle spacing must be maintained while preparing the injection suspension through agitation or other methods. One such method would be to encapsulate the magnetic particles in a starch coating sufficiently thick to reduce the magnetic attraction to near-zero values. Approximately 10 to about 100 $\mu$m thick coatings would be required for 1 $\mu$m magnetic particles. Preparation of the injection suspension would follow the same process described above.

Once the cancer-binding magnetic material has been injected and sufficient time for differentiation to occur has elapsed, the magnetic material must be magnetized. This is assuming demagnetized particles were used in the process. For cases where magnetized particles are required, magnetizing the particles is not necessary. An additional benefit to magnetizing the particles after differentiation is that only the magnetic material in specific areas of the body will be magnetized. This will dramatically reduce the background for detection and imaging, but will also limit energy deposition in areas where none is desired. Magnetization of permanent magnet materials such as Sm—Co and Nd—Fe—B compounds is a very nonlinear process. Particles that receive only 80% of the saturation field will be magnetized to a level significantly below 0.8 of the maximum field. Thus, by using carefully shaped fields to perform the magnetization, one can be very selective in the regions of the body where the magnetic materials will be magnetized. In addition, the magnetization field need only be a pulsed field and can be constructed in the same apparatus as a time-varying field device.

Sub-nanogram quantities of magnetic materials can be detected by superconducting quantum interference device (SQUID) sensors, currently used to measure the weak biomagnetic fields from the brain, heart and other organs. Any localized concentrations of magnetic material after injection by the cancer-binding magnetic particles will identify tumors with an extremely high confidence because of the tumor specificity of the agent being used.

It has been previously shown that minute quantities of magnetic materials in biological systems can be readily measured with SQUID sensors. Kirschvink has reported that magnetite can be found in many animal species, including humans, and in many of the organs, including the human brain, again using SQUID sensors. Kirschvink et al. reported measuring as little as 0.4 nanograms (ng) of magnetite in the human brain (see, Proc. Natl. Acad. Sci., "Magnetite biomineralization in the human brain", vol. 89, pp. 7683–7687, 1992). Highly sensitive magnetoencephalography (MEG) systems are known and have been developed to localize magnetic sources in the brain (originating from brain activity) having a resolution better than a volume element of 1 cm$^3$ where the magnetic field strength at the sensors 10 to 50 fT (femtoTesla=$10^{-15}$ Tesla). This same technology will be used to localize concentrations of magnetic material in tumors where the signals are anticipated to be >1 pT (picoTesla = $10^{-12}$ Tesla) or more than 20–100 times stronger than the signals from the brain. This will translate to better signal-to-noise and better localization resolution.

The method previously used to localize sources can be further improved by using external pulsed alignment fields out-of-phase with the SQUID measurements. This method applies a relatively weak (<100 G) external field to the subject for 100–1000 milliseconds (ms). The field is then turned off for a similar period of time during which the SQUID sensors will observe the relaxation (or randomization) of the magnetic particles after the aligning field is removed. Another permutation of this method is to apply the aligning field normal to the SQUID sensors for 100–1000 ms. The aligning field is turned off and a second field that is tangential with the SQUID sensors is applied as the sensors are activated. The magnetic particles will realign to the new field with a relaxation time that will be proportional to the applied field. This relaxation will be measured by the SQUIDs and can be repeated many times to acquire a statistical measurement that significantly improves the signal-to-noise. The two techniques described here will enhance the sensitivity of the signal dramatically enabling the detection of a small fraction of a nanogram of magnetic material.

The detector system will utilize SQUID sensors, the most sensitive magnetic field sensors known, to detect the very small magnetic fields from concentrated contrast agents. Furthermore, systems with planar and hemispherical sensor array configuration have been fabricated and tested and can be readily used in the present invention using SQUID-magnetometers recently developed for extremely weak field biomagnetic applications.

The magnetic field expected at a SQUID sensor has been calculated as a function of magnetic particle concentration in a tumor. As a baseline, experimentally determined values have been used for concentration of cancer binding agents in breast tumor and relative tumor/healthy tissue concentrations. These results were obtained from a typical scintigraphy experiment using $Tc^{99m}$-sestimibit.[19] The number of $Tc^{99m}$ atoms delivered to a tumor was calculated to be $3.5 \times 10^{11}$ based on experimentally observed decay rates. The total quantity of injected $Tc^{99m}$-sestimibi is limited by the allowable radiation dose a subject may receive during the scintigraphy procedure. If a nonradioactive material were being used, the allowable total injected dose would be much greater and ultimately limited by toxicity concerns. Therefore, the calculated number of delivered $Tc^{99}$m to the tumor ($3.5 \times 10^{11}$ atoms) may be much higher for nonradioactive materials such as magnetic particles.

Table 1 tabulates the results of calculating magnetic field strength at a SQUID sensor that is located 5 cm away from magnetic particles that are clustered within a 1 mm$^3$ volume. The first calculation is for molecular magnetite, which maintains a magnetization in many molecular forms. Assuming sestimibi (or some other cancer binding agent) can deliver the same number of magnetite molecules as has been demonstrated for $Tc^{99m}$ atoms, the magnetic field at a SQUID sensor located 5 cm away from the tumor would be 330 fT, well above the noise floor for SQUID sensors. If the same number of nano-particles of magnetite were delivered to a tumor, the resulting field at the SQUID sensor would be 80 nT (nanoTesla=$10^{-9}$ Tesla) or more than a million times greater than the detection threshold.

The last three calculations (rows) in Table 1 are based on a desired field at the SQUID sensor of 1 pT that would result in a strong signal. For the purposes of this calculation, a particle size of 10 nm radius was used. This size particle is roughly the smallest attainable particle for rare-earth magnet materials (REM). An extremely conservative remnant field value for the REM material of 3 kG (kiloGauss) has been used in these calculations. Both Nd—Fe—B and Sm—Co materials are commonly available with remanant field values in excess of 10 kG for multicrystalline particles. It is found that only a million magnetite particles are required to produce an easily observed 1 pT field. Biolocially, this is an extraordinarily small number of particles for a 1 mm tumor where over 10$^9$ binding sites would be expected. When the magnetite is replaced with REM materials, as little as 14,000 particles with a 10 nm radius are needed to detect the tumor. The treatment phase of MCT requires larger particles, and calculations show that very few 100 nm particles are needed to produce an easily detected and localizable field. The detection threshold is far below the number of particles for effective therapy, thus the detection and localization are clearly attainable.

TABLE 1

|   | Magnetic Material | Particle Size (radius) | Number of Particles | Field at Sensor (5 cm) |
|---|---|---|---|---|
| 1 | Magnetite | molecular | $3.5 \times 10^{11}$ | 330 fT |
| 2 | Magnetite | 10 nm | $3.5 \times 10^{11}$ | 80 nT |
| 3 | Magnetite | 10 nm | $3 \times 10^6$ | 1 pT |
| 4 | REM | 10 nm | $3 \times 10^4$ | 1 pT |
| 5 | REM | 100 nm | $3 \times 10^1$ | 1 pT |

Several successful approaches for magnetic source localization based on magnetic measurements have been developed for MEG and MCG (see, for instance, Huang et al., Electroenceph. Clin. Neurophys. v. 108, pp. 32–44, 1998). Relatively straight forward adaptation of these algorithms to the breast geometry will be required. It is anticipated that MCT source localization will be substantially better than MEG localization of cortical sources (about 5 millimeters), because the geometry and structure will be far simpler and sources are expected to be substantially stronger. Preliminary modeling estimates (using the modeling code developed and described by Flynn in Rev. Sci. Instrum., v. 65, pp. 922 (1994) to estimate source localization accuracy) for localization in a flattened breast geometry indicate better than 1–2 mm localization precision should be expected using ~400 fT signal amplitudes, and 6/1 tumor/healthy tissue concentration ratio. The modeling code estimates the same localization precision for a 6 cm radius hemispherical breast and source strength of 1 pT. One should note that sensitivity to sources is independent of size (e.g. SQUID sensors can detect a micrometer magnetic source, but can only localize the source to within ~1 mm in space). Extended sources (for large or distributed tumors) will also be amenable to more sophisticated codes to examine the physical extent of the sources.

There are three primary mechanisms for energy (heat) deposition into tissue by magnetic stimulation of the in vivo magnetic particles. These include: ohmic heating; hysteretic heating; and, viscous heating.

Ohmic heating is the heat that results from electrical eddy currents flowing in the resistive magnetic particle material. Eddy currents are generated by the time-varying magnetic field according to the laws of induction (Maxwell's equation). Ohmic heating is probably only practical for larger (macroscopic) objects with moderately high conductivity, thus it is not a significant mechanism for heating the magnetic particles used in MCT. The eddy currents generated in tissue will provide constraints for amplitude, frequency, and duration of application of the external magnetic field. The specific absorption rate (rate of energy deposition) for ohmic heating of a material in a time-varying magnetic field, SAR(O) is given by:

$$SAR(O) = 0.5 \cdot (\pi \cdot \mu \cdot H \cdot \nu \cdot D)^2 \cdot (\sigma/\rho) \qquad \text{(Equation 1)}$$

The SAR(O) is calculated separately for each region and material. $\mu$ in Equation 1 is the permeability of the material that is being "heated." For most non-magnetic materials (such as tissue), $\mu \approx \mu_0 = 4\pi \times 10^7$ Vs/Am. For the permanent magnet materials of interest for MCT, typical values of $\mu = 1.005 - 1.01\ \mu_0$. H is the amplitude of the external applied time-varying magnetic field. $\nu$ is the frequency of the time-varying magnetic field. D is the cross-sectional diameter of the region being heated. $\sigma$ is the electrical conductivity of the material. $\rho$ is the density of the material.

Hysteretic heating is the heat that is generated when a magnetic material (e.g. permanent magnet) is forced around part or all of the hysteresis loop (magnetization curve). As the external magnetic field changes phase (direction), some part of the applied field will oppose the direction of the magnetic particles. The practical effect is to produce heat as the external field attempts to reverse the field of the magnetic material. The specific absorption rate (rate of energy deposition) for hysteretic heating of a material in a time-varying magnetic field, SAR(H) is generally given by:

$$SAR(H) = (2\pi^2/kT) \cdot (V\tau_N/\rho) \cdot (\mu_o \cdot M_S \cdot H \cdot \nu)^2 \cdot (1/1 + (2\pi \cdot \nu \cdot \tau_N)^2) \qquad \text{(Equation 2)}$$

However, this expression assumes that the saturation magnetization of the permanent magnet is less than the external applied field. For this case, this is not true. A typical applied field will be ~1 kG whereas the saturation magnetization for Sm—Co and Nd—Fe—B are in excess of 10 kG. Thus, the SAR(H) for MCT would be:

$$SAR(H) = (2\pi^2/kT) \cdot (V\tau_N/\rho) \cdot (\mu_0 \cdot H^2 \cdot \nu)^2 \cdot (1/1 + (2\pi \cdot \nu \cdot \tau_N)^2) \qquad \text{(Equation 3)}$$

where $\tau_N = \tau_0 \cdot \exp(\Delta E/kT)$ is the Neel relaxation time and $\tau_0 \approx 10^{-9}$ sec, $\Delta E = K \cdot V$, K is a material parameter (typically $10^3$ to $10^4$ J/m$^3$, though it can vary widely), and V is the particle volume. In Equation 3, k=Boltzmann's constant, T is the nominal temperature (in Kelvins), and all other quantities are defined after Equation 1. The important fact to note about Equation 3 is that the SAR scales with $H^2$.

Viscous heating is the heat that is generated by the kinetic motion of a particle within a viscous fluid. Magnetic particles or samples will attempt to rotate to a position aligned with the applied external field. This position is the lowest energy state for the system. As the particles begin to rotate toward the lowest energy state (aligned with the external field) in a viscous medium, energy will be deposited in the medium. The specific absorption rate for rotational motion of very small magnetic particles in a viscous fluid under the influence of a time-varying magnetic field, SAR(V) is given by:

$$SAR(V) = (2\pi^2/k \cdot T) \cdot (V\tau_B/3\rho) \cdot (\mu_0 \cdot M_S \cdot H \cdot \nu)^2 \cdot (1/1 + (2\pi \cdot \nu \cdot \tau_B)^2) \qquad \text{(Equation 4)}$$

where $$\tau_B \approx 6 \cdot \eta \cdot V_B/k \cdot T \text{ is the Brownian relaxation time} \qquad \text{(Equation 4a)}$$

Where $\eta$ is the fluid viscosity and $V_B$ is the total particle volume including non-magnetic coatings and shells. In Equation 4, the $M_S$ is the saturation magnetic field and does not reduce to the applied magnetic field in this case because it represents a coupling between the two fields $M_S \cdot H$. V in Equation 4, as in Equations 1–3, is the volume of the magnetic material portion of the particle itself. All other terms in Equation 4 are defined above.

In summary, it is noted that the total SAR for the magnetic particles will be a combination of ohmic, hysteretic, and viscous heating. Compare Equations 3 and 4 and note that the relative contribution of viscous to hysteretic energy deposition can be written:

$$SAR(V)/SAR(H) \approx [\tau_B/3\tau_N] \cdot [(M_S \cdot H)^2/H^4] \qquad \text{(Equation 5)}$$

The Neel relaxation time, $\tau_N$, is typically on the order of microseconds ($10^{-9}$) but is dependent on particle properties (shape, size, material, etc.) and varies widely over several orders of magnitude. The Brownian relaxation time, $\tau_B$, as defined by Equation 4a is equal to approximately 1 ms (millisecond) for a 100 nm particle in a medium with viscocity equal to water ($\eta = 10^{-3}$ Js/m$^3$). Thus, the first ratio in Equation 5 favors the viscous energy deposition for many, if not most particle types. The second ratio reduces to $(M_S \cdot H)^2/H^4 = (M_S)^2/H^2$. For a typical MCT design using REM magnetic particles, $M_S$ is typically between 7 and 10 kG and H can be designed to reach 1 kG. Thus, the viscous energy deposition is favored by a factor of 50 to 100. Consequently, it is expected that SAR(V) will be the dominant mechanism for energy deposition, accounting for between 90 and 99% of the total energy deposited for the MCT approach. Thus, it will be recognized that hysteretic heating makes an additional minor contribution to the overall heating The magnetic material can be administered to a subject internally, e.g., orally, parenterally, e.g., intravenously, intramuscularly, subcutaneously, topically and the like, depending upon the nature and location of the tumor. Dosage and frequency of administration may also vary depending upon the nature of the tumor as can be routinely determined.

The quantity of the magnetic material attached to the chemical or biological species that needs to be delivered to a subject is dependent upon the ratio of material that goes to the desired location in comparison to the amount that goes to other locations (e.g., differentiation between tumor and healthy tissue). The amount going to the desired location must be sufficient to yield the needed magnetic field either by inherent or induced field.

In one embodiment of the present invention, the magnetic material of the magnetic material containing substance is demagnetized prior to administration to a subject. After the demagnetized magnetic material is allowed to reach the targeted tissue or cells, e.g., tumor cells, the material can be selectively magnetized by application of a strong pulsed field. In this manner, any problems with possible agglomeration of magnetic material during the administering of the material can be minimized or eliminated.

Once a malignant tumor is identified and localized, generated thermal energy is used to induce substantial or complete necrosis of the tumor cells with minimum collateral damage of healthy tissue. Modeling studies have been conducted that indicate that inductive heating (as described by Gordon in the various patents listed above) will not yield the temperature rise necessary to cause necrosis. In contrast, the same modeling studies have pointed to viscous heating as attaining the required temperatures. The thermal energy will result in sufficient hyperthermic treatment to result in substantial or complete necrosis of the tumor cells through viscous heating. Viscous heating is the result of movement within the medium as by, e.g., a stirring effect. By appropriate manipulation, sufficient local heating of more than 10° C. within a few seconds is possible whereafter substantial or total necrosis within the localized region of the magnetic material can be induced. It is known that as little as a 10° C. increase in cell temperature can result in death of a cell. The temperature is raised to the minimum level necessary to destroy the desired cells. Activation fields of about 100 to 1000 Gauss (0.01 to 0.1 Tesla) are employed to locally heat the selected region. The region can be measured by standard infrared sensors or by an in situ thermometer using Barkhausen noise associated with magnetic domains delivered to such selected tissue. Such Barkhausen noise can be measured by conventional squid technology.

Once a tumor is localized, the most compelling feature of the MCT technique is that immediate therapy to eradicate the tumor can be implemented. The MCT technique enables the physician to rapidly deposit thermal energy at the tumor site, inducing complete necrosis of the tumor cells with minimal collateral damage of healthy tissue.

The basis of the treatment concept is depositing sufficient energy into the tumor to cause rapid and complete cell necrosis (death) with minimal collateral damage to healthy tissue. The energy is produced by coupling an external time-varying magnetic field to the in vivo magnetic particles. Energy is deposited into the tissue via ohmic, hysteretic, and viscous heating mechanisms. Each of these is described in detail. Absolutely no microwave radiation or any form of ionizing radiation is involved in this process. Heating mechanisms are broadly referred to as hyperthermic methods.

Hyperthermic methods commonly in use and reported in the medical literature use relatively large magnetic cylinders inserted into the region of a tumor and apply external time-varying magnetic fields. Heating by this form of large implanted magnetic needle is dominated by hysteretic effects. The parameters needed to induce substantial ohmic heating would result in an intolerable heating of the healthy tissue within the magnetic field because of the fairly high tissue conductivity. Viscous heating is not a factor because the implant size prevents movement of the needles by the external magnetic field. The low efficiency of hysteretic heating only allows the tissue to be heated slowly resulting in large "tails" in the thermal distribution. Using this technique for tumor cell necrosis (killing the cells) would cause substantial collateral tissue damage.

In contrast to traditional hyperthermic therapy, MCT allows rapid thermal deposition to a local area preventing significant heating of regions far from the specific tumor site. This is a consequence of the small particle size and the large magnetization of the particles. The rate of energy deposition by viscous heating for high remnance magnetic materials, such as Sm—Co and Nd—Fe—B, is as much as an order of magnitude greater than for the hysteretic heating mechanism.

Attaining the equivalent density of labeled cancer-binding compounds required to deposit sufficient energy for cell necrosis in tumors has already been demonstrated by the sestimibi results. However, additional concentration of particles can be realized by using stable (nonradioactive) materials in place of the $Tc^{99m}$. As noted above, larger magnetic doses can be administered, limited only by any (possible) chemical toxicity of the agent. Ultimately, further magnetic particle concentration can be realized by direct injection to the localized tumor site. Although, based on the results of the sestimibi study, it is not likely that additional directly injected magnetic material will be indicated. The only case where direct injection may be indicated is for larger tumors with necrotic cores that have little or no vascularization to carry sufficient targeting agents into that region.

Attaining the maximum differentiation (ratio of cancer binding agent concentration in tumor tissue compared to healthy tissue) in tissue is crucial to minimizing collateral damage due to heating of healthy tissue. Studies for many cancer binding agents and determination of maximum differentiation are performed using radiopharmaceuticals. Consequently, the radioactive half-life of the radiopharmaceuticals limits the term of these studies. The biological half-life of tumor binding agents (e.g. sestimibi) is often larger in tumor tissue than healthy tissue. Therefore, one may need to reevaluate the optimal time for both detection and therapy phases of MCT in accordance with the use of stable agents. By using stable labels, a wait period of any reasonable time may be used to optimize both the detection and the differentiation of magnetic particles between tumor and healthy tissue.

The physics that governs thermal deposition by external excitation of the magnetic particles clearly suggests that larger particles will be more efficient in energy deposition. However, the size of the magnetic particles is limited by the maximum particle size the human renal system can readily pass, typically a few hundred nanometers at most if the particles can not be metabolized (broken down) by the body.

The present invention further contemplates the use of magnetic particles with a size designed to optimize thermal deposition without obstructing the renal system. Certain magnetic materials (e.g. iron-oxides and neodymium-iron-boride) will oxidize ablatively and decompose in the body (in vivo) far too rapidly to be used for MCT without additional isolation from biological and chemical attack. An easily oxidized magnetic material (Nd—Fe—B) can be coated with a material that prevents the oxidation and does not itself attack that magnetic material. The coating will be selected to slowly dissolve (through either chemical or biological attack) in vivo, such as coatings used for time-released medications. The coating will protect the magnetic particles for a specified period of time after which the particle will decompose rapidly. The oxidized products will be metabolized and will consequently not obstruct the renal system.

A time varying spatial distribution of the magnetic field is desired. This is accomplished by either physical movement of coils or magnets or by a rotation of the field distribution by a set of computer controlled magnetic induction coils that are distributed and phased to produce the desired field distribution and rotational frequency.

Figure 1:
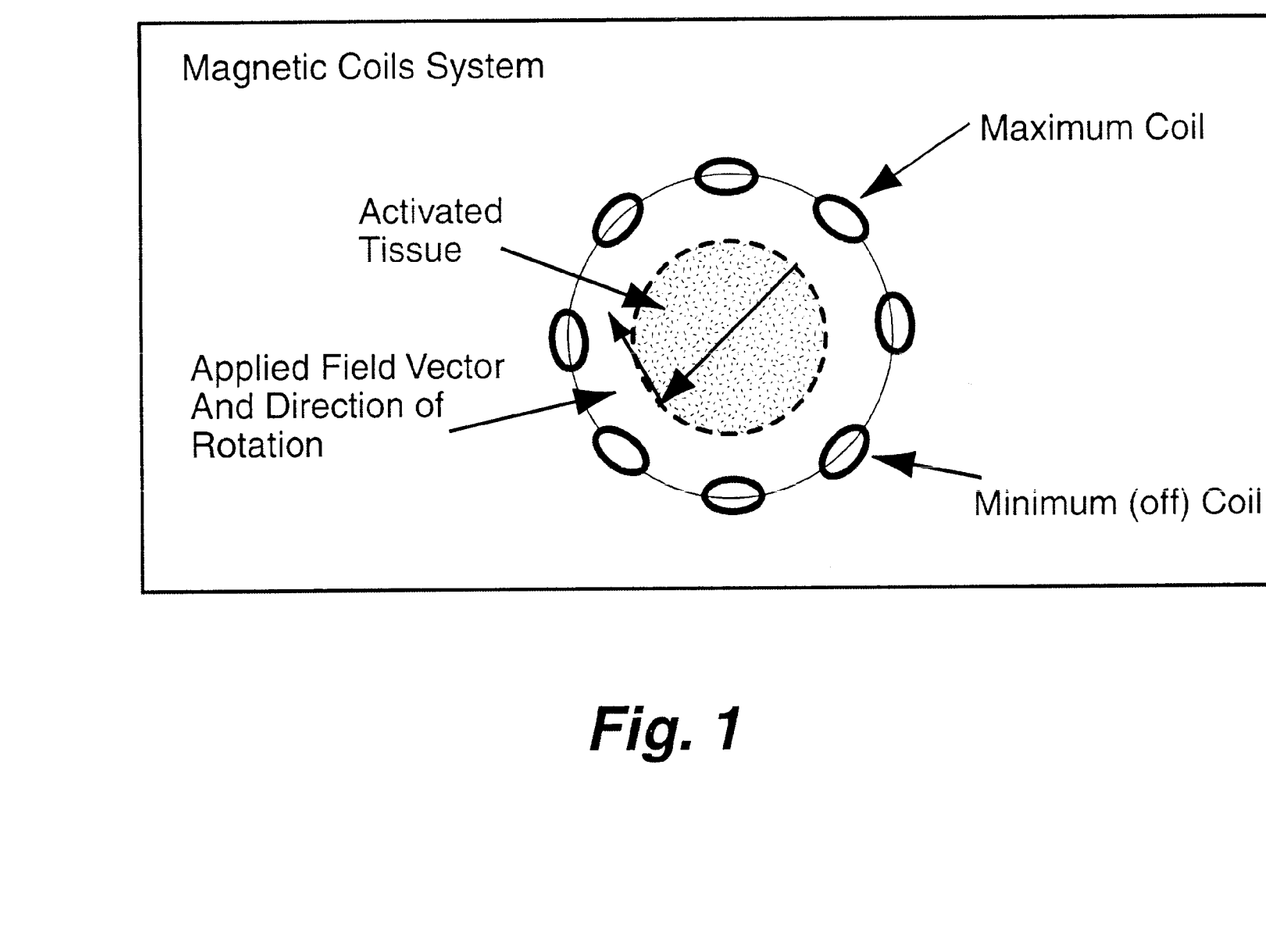
FIG. 1 depicts a schematic drawing of a coil system for application of a time-varying external magnetic field in accordance with the present invention.

The method of applying the external time-varying magnetic field is as follows. A simple schematic of a coil system that can be used to apply the time-varying external magnetic field is shown in FIG. 1. Four pairs of magnetic field coils (more may be used to attain desired field uniformity and control) are arranged on a circle. Each pair consists of coils on opposite sides of the circle and is activated together. The desired field profile is a relatively uniform field that rotates in a circle. This is accomplished by computer control of the coil sets to apply a time varying current to each pair of coils in a sinusoidal fashion (e.g. smoothly varying current profile). FIG. 1 shows a "snapshot" of the device at some moment when one pair of coils are at the peak of the current waveform, another pair of coils are at a minimum, and other pairs of coils are intermediate. The rate at which the current varies to each coil pair is identical, but each coil pair is out of phase from it's neighbors by $2\pi/N$ where N is the number of coil pairs.

In the rotating magnetic field described immediately above, the magnetic particles will precess with the rotating external field in an attempt to maintain the lowest possible energy state (e.g. perfectly aligned with the applied field). In a non-inertial and non-viscous medium, the particle would remain perfectly aligned with the external field. In a viscous environment, however, the particle will experience a drag as it rotates and consequently a phase lag behind the applied field. If the drag is sufficient, the phase lag will continue to increase until the lowest energy state (alignment of particle and external field) is in the opposite direction of rotation. At this point the particle will attempt to rotate "backward" (opposite the direction of rotation of the external field) within the constraints of viscous drag and until the external field "catches up" to the particle. Modeling calculations show that indeed, above a certain frequency (determined by precise fluid viscosity, applied field strength, and strength of the magnetic particles) the particles will "jitter" back and forth rather than perform complete rotations with the external field. Although some predictions break down when the particle is no longer sweeping out full rotations, energy is still deposited in the medium. Although particles may not sweep out a full rotation with each cycle of the external magnetic field, the use of higher frequencies may ultimately be more efficient in the net energy deposited. It is clear that an empirical study would be needed to optimize the system parameters, e.g. for a specific set of parameters, magnetic particles "jittering" in an externally applied magnetic field may deposit more energy than particles performing complete rotations at a lower frequency.

Another system for conducting both the treatment and the temperature measurement of the present invention would include a combination of electromagnetic field generating coils and squid devices. A combination of alternating fields from, e.g., multiple electromagnets, with a phase difference between the fields is designed so as to yield a rotation of the overall field upon the desired body. In effect there would be a stirring action. In this manner the magnetic material would undergo rotation within the rotating field and result in viscous heating of the medium or in this case the cellular area in the vicinity of the body whereat the magnetic material containing substance is attached. Initially, a gradual range of frequencies would be cycled until the correct frequency for a desired stirring rate (heating) is found. Use of the tissue temperature as measured by the Barkhausen noise associated with the magnetic domains may allow for a feedback loop wherein first the fields generate some stirring action for the heating and then the SQUID measurement technique is used to measure the progress of tissue heating and so forth. In contrast to hysteretic heating, such a viscous heating process would employ lower frequency. The frequencies that optimize the rotational (or vicous) heating for maximal energy transfer for each specific system (e.g., type of magnetic material, type of tissue and the like) are generally well below 1 MHz and may be as low as 100 Hz assuming complete particle retention. As noted, jittering may induce higher thermal deposition at higher frequencies. Hysteretic heating is via induction and generally employs high frequencies as described by Gordon et al. in U.S. Pat. No. 5,622,686 as from 1 kilohertz to 100 megahertz.

Use of a weak-magnetic field sensor based on SQUID technology would allow application of smaller amounts of the magnetic material/carrier to a subject. which are needed in order to detect the presence of the magnetic material at a cancer or tumor site for subsequent treatment and for temperature measurements. The amount of magnetic material can vary depending upon the magnetic strength per unit volume of the material and the method used to produce the field. The field can be produced either through inherent magnetization or induced magnetization through an external field.

Magnetic materials such as $Fe_2O_3$ (ferrite), $SmCo_5$, $Sm_2Co_{17}$, and other similar materials have large remnant magnetization, while magnetic materials such as iron (in various forms and complexes) can have a larger magnetization that is induced by application of an external field. The external field needed for this purpose can be readily generated by simple sources (such as permanent magnets or field coils) in the range of 100 Gauss to 1000 Gauss.

One example of a suitable sensor system is a seven channel SQUID second-order gradiometer system as manufactured by BTI, Inc.

Another example of a suitable sensor system is a twelve channel SQUID system as described in a paper by Kraus et al., "First Results for a Novel Superconducting Imaging-Surface Sensor Array", to IEEE Trans. Appl. Superconductivity, (accepted for publication). Details of this paper are described below.

An entirely new multi-channel SQUID gradiometer system, the superconducting imaging-surface gradiometer has been fabricated and tested. A 12-channel system using this design has demonstrated higher performance and lower noise than conventional gradiometer sensor systems. The system also provides additional shielding of background fields, reduced cost, and simpler fabrication techniques than conventional gradiometers. The sensor density and array size can readily be extended, and the geometry of this system is ideal for magnetocardiography (MCG) and related applications.

Current biomagnetic measurements predominantly use gradiometers for almost all applications from magneto-encephalography (MEG) to magnetocardiography (MCG)

and magnetoenterography (MEnG), even inside a shielded room. Gradiometer baselines can be tuned to provide maximum signal-to-noise (SNR) sources of interest. Conventional wire-wound gradiometers are, however, both difficult to fabricate with the required precision and difficult to mount in a sensor system. Furthermore, wire wound gradiometers introduce electrical limitations that increase the inherent sensor noise. The superconducting imaging-surface method simplifies gradiometer design considerably.

The principal application of the array system discussed here is in MCG, while the same superconducting imaging-surface concept is being applied to a whole-head MEG system as well. MCG was first reported in 1963 by Baule and McFee using room temperature pickup coils with several million turns and a ferrite core. The Superconducting Quantum Interference Device (SQUID) was first used for MCG measurements by Cohen et al. in 1969 at MIT. SQUIDs rapidly supplanted room temperature pickup coils for detecting very weak magnetic fields, and are now being used in an ever growing number of applications from biomagnetism and nondestructive testing to geophysical assay and intelligence. Although the extraordinary sensitivity of SQUIDs lowers the threshold for magnetic field sources one can detect, it also increases the sensitivity to noise from ambient field sources requiring the use of shielded rooms and gradiometers. The typical first-order SQUID gradiometer consists of a set of superconducting pickup loops wound in opposition that are sensitive to the difference (derivative) of the field in a specific direction while canceling the uniform component of the field. Winding gradiometer coils requires extraordinary precision to optimize uniform field cancellation (balance) and prevent introducing field distortions. The superconducting imaging method completely avoids this difficulty.

Figure 2:
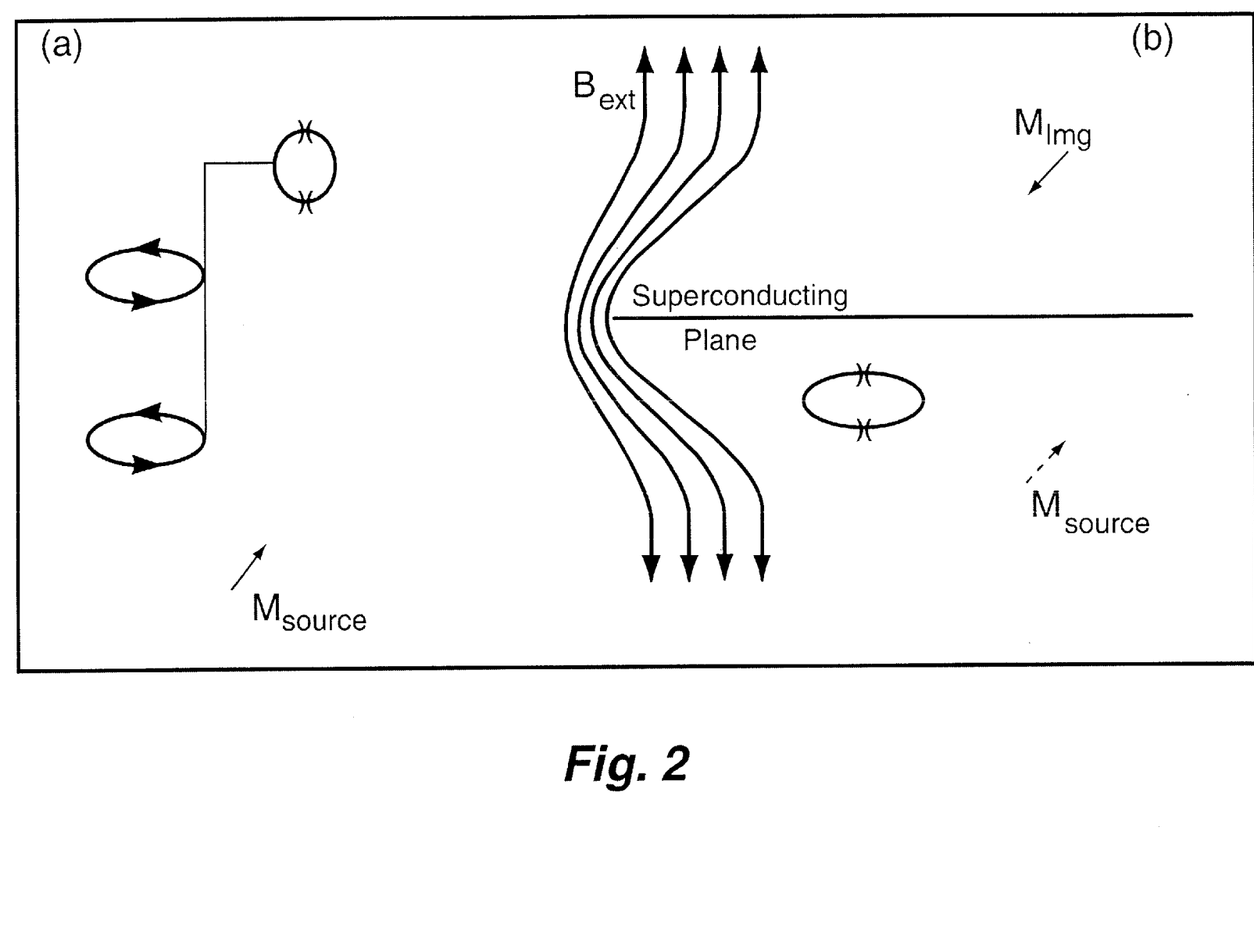
FIG. 2 depicts both a conventional axial gradiometer coil and a superconducting imaging-surface gradiometer using a flat (planar) imaging surface.

FIG. 2 depicts both a conventional axial gradiometer coil and a superconducting imaging-surface gradiometer using a flat (planar) imaging surface. FIG. 2a illustrates the currents in a conventional gradiometer coil resulting from the magnetic dipole source shown. FIG. 2b illustrates how the superconducting imaging-surface gradiometer (with a flat imaging surface) responds to both nearby sources and uniform ambient fields. A magnetic source, $M_{source}$, causes Meissner currents in the superconductor that can be represented by an image source, $M_{img}$, identical to $M_{source}$ except located behind the imaging plane with opposite sign of the field component perpendicular to the imaging plane. The SQUID magnetometer, shown on the source side of the imaging plane, measures the flux resulting from the superposition of fields from both $M_{source}$ and $M_{img}$. This superposition of fields at the SQUID magnetometer is identical to a gradiometer with one pick-up loop located at the magnetometer, and the second pick-up loop spaced behind the imaging plane at a distance equal to the magnetometer-imaging plane separation. The superconducting surface also provides a natural shield from ambient magnetic fields. Magnetic field lines, $B_{ext}$, are excluded from the superconductor and ambient field lines wrap around the superconductor as shown in FIG. 2b, providing a measure of shielding from ambient fields for sensors relatively close to the plate.

The theory for superconducting imaging gradiometry was first described by van Hulsteyn et al. They showed that analytic expressions could only be derived for unconstrained geometries (e.g. those without end). An analytic imaging expression for the flat 12-channel image-surface system must therefore assume an imaging surface of infinite extent. This assumption is justified for magnetic sources where the source-to-imaging-surface distance is much less than the distance from the source to the edge of the imaging surface. Thus, sources that are much closer to the imaging surface and/or the sensor than to the real edge of the imaging surface should be adequately described by the analytic formalism of van Hulsteyn.

The theory holds only for ideal superconductors, consequently any material defects, impurities, or improper cooling of the imaging-surface that would cause significant flux trapping will distort the source image, resulting in an imperfect gradiometer. Therefore, careful consideration must be given to the choice, fabrication, final treatment, and cooling of the imaging surface. Initial confirmation of the imaging principle was attained using a single channel SQUID with a pickup coil, located in front and behind a five centimeter diameter lead imaging surface. A gradiometer response was observed for a small source passed in front of the coil with a rejection factor of ~350,000 for uniform fields in a large Helmholtz coil using an analog lock-in amplifier.

A flat SQUID-array system has now been constructed utilizing 12 thin-film button SQUIDs that were specifically designed for this effort by Conductus, Inc. in collaboration with and under contract to Los Alamos for use in image-surface systems. The resulting design integrated both the SQUID circuit and the superconducting pickup loop on a single monolithic device using a niobium lithographic technique. The SQUIDs have extremely low noise characteristics that are extremely stable over time. This button SQUID-magnetometer combined with the source imaging of the superconducting plane generates total fields equivalent to a gradiometer as described above. The result is an axial gradiometer fabricated entirely using a lithographic process, relatively simple and inexpensive to fabricate, and simple to install into sensor arrays. In the present system, 12 fT/√Hz at 10 Hz and 10 fT/√Hz at 100 Hz noise levels were observed with the system located in a moderately shielded chamber. A flat unshielded noise level of ~1 pT/√Hz was observed between ~1 Hz and 1 kHz in a very (electrically) noisy laboratory.

The SQUID-magnetometers are co-planar and spaced at 2-cm intervals in two rings around a center point. The inner circle consists of four sensors and the outer circle, eight. The sensors are mounted on cryogenically rated fiberglass tubes that are precisely and rigidly held in place by a spacer disk. This disk maintains the separation and relative parallelism between the sensors and the superconducting between the two fiber-glass disks. Some measurements included two additional sensors on the "back" side of the imaging surface located directly opposite two of the 12 sensors on the "front" (source) side of the imaging plane, one on the inner circle and one on the outer circle. The various configurations of the 12-channel system allowed us to test the essential aspects of the imaging-surface concept including button SQUID-magnetometer performance, imaging surface materials (lead and niobium), and experimental validation of imaging theory.

The button SQUIDs are located 2 cm from the 25 cm diameter imaging-plate resulting in an equivalent 4 cm baseline image-surface gradiometer. The 12-channel system has performed reliably with all channels functional. Data was acquired for performance measurement using the PC-SQUID™ multichannel electronics designed by Conductus for these SQUIDs.

The integrated structure has proven to substantially reduce noise over other magnetometer coils. The field noise observed for a typical lithographed sensor is 2 to 3 fT/√Hz, extremely low for a large area SQUID magnetometer. The transfer function, on the order of 300 $\mu V/\Phi_0$, eliminates the need for a low-temperature matching transformer. The integrated lithographed design also results in a small and simple disc-shaped package containing the entire assembly. Four small soldering pads on both sides of the fiberglass disk connect the SQUID device and a heater to the room temperature electronics.

The theoretically expected shielding factor for this system can be easily estimated as 25/2=12.5, the aspect ratio of imaging radius to sensor baseline, at the center of the imaging surface. Thus, background noise in an unshielded environment will only be screened by about a factor of ten and will likely dominate the noise spectra, as observed. A phantom was constructed consisting of 12 sets of three orthogonal magnetic dipoles that can be activated by an external signal generator. To verify the imaging theory, the phantom source field was measured at the sensors as a function of phantom distance from the sensor array. Selected sets of these data where the Meissner where the measured field at the sensors was plotted as a function of phantom source distance from the imaging plane and compared with the theoretical imaging gradiometer falloff with distance. The data shown for the $B_z$ phantom placed slightly off-center of the pattern of SQUID sensors. The inner ring of sensors were designated SQUID channels 1–4 and the outer ring were channels 5–12 agree very well with predicted values, indicating the system is behaving as a gradiometer in accordance with theory. Further no deviation was observed from the analytic expressions, for the constrained geometry, even for sources many centimeters away from the imaging surface. Qualitatively, significant deviation was observed from the gradiometric behavior predicted by the analytic formulas only when the phantom source was both near the edge of the imaging plate and spaced away from the surface.

The same measurements were made for both lead and niobium imaging plates and the same result was obtained for most sensor locations. For one case, however, the plot of measured field as a function of phantom source distance clearly diverted from theory. The noise characteristics and frequency response of the SQUID appeared normal leading us to attribute the variation to an imperfection in the niobium. Inspection of the niobium showed no observable defect in the plate. The conclusion is that there is no basic difference between type I and type II superconductor performance for this configuration, however there appears to be a greater sensitivity of niobium to inclusions and stresses. The measurements required to determine the observed differences between the lead and niobium imaging surfaces are outside the scope of this effort. Measurements without an imaging plane were difficult because the reduced shielding made it ifficult to keep the SQUIDs locked. These measurements could not be made in the shielded can because the field from the phantom coil was severely distorted by eddy current and remnant effects of the shielding can.

The imaging characteristics of SQUIDs located on the "back" side of the 12-channel flat imaging surface were also measured. SQUIDs located behind the imaging surface sense background fields that would be used for software or analog background cancellation. These measurements were performed to determine background sensor sensitivity to phantom sources, and the symmetry of the sensor sensitivity to uniform fields (sensors on the front and back of the imaging plane should measure the same for a uniform field). Any sensitivity of the background SQUIDs to phantom fields would have the undesirable effect, when software or analog background cancellation was implemented, of canceling a portion of the signal of interest. The symmetry of the sensor sensitivity to uniform fields will be used for developing the analog and software algorithms for background field cancellation and compared with theory at a later date. All measurements reported used the lead imaging plane. Measurements of the source shielding from the background sensors will be used as an additional correction for software background subtraction.

Measurement of the symmetry of sensor sensitivity to uniform fields followed theoretical predictions on the basis of first principles. This observation is dependent on the same imaging characteristics for both sides of the imaging plate and would not hold for geometries other than flat plate. It confirms, however, the fact that the 12-channel imaging plane is operating according to theoretical expectation.

Finally, the system was placed in the uniform field region of a large double Helmholtz coil and the rejection factor for uniform (i.e. distant) fields was measured to be a factor of 11 for the SQUIDs on the inner circle and 8 for those on the outer. These observations very closely match expectations based on first principles.

Fabrication and preliminary testing of a 12-channel SQUID array using the superconducting image-surface gradiometer concept has been completed. Sensor response to "point dipole" magnetic sources, and uniform fields used to simulate ambient magnetic fields followed predicted values to high precision. Edge effects were not observed for sources, within 5 cm of the center of the imaging surface independent of whether the source is close or far from the surface. The superconducting imaging-surface also reduced uniform ambient fields at the SQUID sensors by approximately a factor of ten. Finally, a high degree of symmetry was observed between sides of the imaging surface for uniform fields. This symmetry, along with the low sensitivity of sensors on the back side of the imaging-surface to sources close to the front side, provides an excellent circumstance for implementing either digital or analog background rejection.

The goal is to implement a higher density array with the superconducting imaging surface, together with background rejection, and utilize this system for MCG and other biomagnetic studies.

Although the present invention has been described with reference to specific details, it is not intended that such details should be regarded as limitations upon the scope of the invention, except as and to the extent that they are included in any accompanying claims.

What is claimed is:

1. A method of detecting and treating tumors within a subject comprising:

administering a dosage of magnetic material containing substance to a subject, said magnetic material containing substance adapted for preferential attachment to tumor cells;

detecting location within said subject of said magnetic material containing substance attached to tumor cells by use of a sensor array including superconducting quantum interference devices; and, manipulating by a low frequency field said magnetic material within said subject such that said magnetic material containing substance undergoes heating whereby tumor cells having said attached magnetic material are heated sufficiently to cause selective necrosis of at least a portion of said tumor cells, wherein said manipulating magnetic material within said subject includes applying a rotational field to selected portions of said subject whereby said magnetic material containing substance undergoes a rotation to yield viscous heating.

2. A process for the non-invasive measurement of tissue temperature within a subject comprising:

administering a dosage of magnetic material containing substance to a subject, said magnetic material containing substance adapted for preferential attachment to selected tissue;

measuring Barkhausen noise associated with magnetic domains delivered to such selected tissue; and, correlating a tissue temperature with said measured Barkhausen noise.

3. The process of claim 2 wherein said non-invasive measurement of tissue temperature is employed in a feedback loop for the detection and treatment of tumors within a subject.

* * * * *

UNITED STATES PATENT AND TRADEMARK OFFICE
CERTIFICATE OF CORRECTION

PATENT NO. : 6,470,220 B1
DATED : October 22, 2002
INVENTOR(S) : Kraus et al.

Page 1 of 1

It is certified that error appears in the above-identified patent and that said Letters Patent is hereby corrected as shown below:

Title page,
Item [56], References Cited, insert -- OTHER PUBLICATIONS
Flynn, Edward R., "Small Business Innovation Research (SBIR) Progam," Phase I Grant Application, submitted to Department of Health and Human Services, August 3, 1998. --

Signed and Sealed this

Second Day of August, 2005

JON W. DUDAS
*Director of the United States Patent and Trademark Office*